United States Patent [19]

Landa

[11] 4,264,205
[45] Apr. 28, 1981

[54] RAPID SCAN SPECTRAL ANALYSIS SYSTEM UTILIZING HIGHER ORDER SPECTRAL REFLECTIONS OF HOLOGRAPHIC DIFFRACTION GRATINGS

[75] Inventor: Isaac J. Landa, Wheaton, Md.

[73] Assignee: Neotec Corporation, Silver Spring, Md.

[21] Appl. No.: 940,360

[22] Filed: Sep. 7, 1978

Related U.S. Application Data

[63] Continuation-in-part of Ser. No. 825,155, Aug. 15, 1977.

[51] Int. Cl.³ .............................................. G01J 3/12
[52] U.S. Cl. ..................................... 356/326; 356/334
[58] Field of Search ................ 356/326, 332, 108, 97, 356/95, 186, 96, 189, 334; 358/195; 350/315

[56] References Cited

U.S. PATENT DOCUMENTS

| | | | |
|---|---|---|---|
| 2,602,368 | 7/1952 | Barnes | 356/189 |
| 2,679,013 | 5/1954 | Barnes | 307/106 |
| 3,447,873 | 3/1966 | Ashley et al. | 356/334 |
| 3,472,595 | 10/1969 | Hashizume | 356/96 |
| 3,563,656 | 2/1971 | Helms | 356/96 |
| 3,614,227 | 10/1971 | George | 356/95 |
| 3,765,775 | 10/1973 | Ganssle et al. | 356/188 |
| 3,836,254 | 9/1974 | Barringer | 356/74 |
| 3,861,788 | 1/1975 | Webster | 350/315 |
| 3,877,818 | 4/1975 | Button et al. | 356/186 |
| 3,885,879 | 5/1975 | Louder et al. | 356/189 |
| 4,030,828 | 6/1977 | Sonobe et al. | 356/189 |
| 4,030,829 | 6/1979 | Hooper | 356/97 |
| 4,054,389 | 10/1977 | Owen | 356/189 |
| 4,068,954 | 1/1978 | Da Silva | 356/100 |
| 4,070,111 | 1/1978 | Harrick | 356/83 |

Primary Examiner—John K. Corbin
Assistant Examiner—B. W. de los Reyes
Attorney, Agent, or Firm—Lane, Aitken, Ziems, Kice & Kananen

[57] ABSTRACT

An improved optical system is disclosed for rapid, accurate spectral analysis of the reflectivity or transmissivity of samples. A concave holographic diffraction grating oscillated at high speed is utilized to provide a rapid scanning of monochromatic light through a spectrum of wavelengths. The grating is positively driven at very high speed. The rapid scan by the grating enables the reduction of noise error by averaging over a large number of cycles. It also reduces the measurement time and thus prevents sample heating by excessive exposure to light energy. A filter wheel having opaque segments is rotated in the optical path and is synchronous with the grating. The filter wheel is divided into two arcuate segments separated by the opaque segments arranged approximately 180 degrees apart. One arcuate segment of the wheel transmits only first order light. The other arcuate segment transmits only second order light. Separate photodetectors are employed during infrared analysis of samples for detecting first order and second order wavelength transmissions and an electronic decoder apparatus is utilized for switching between detectors.

12 Claims, 10 Drawing Figures

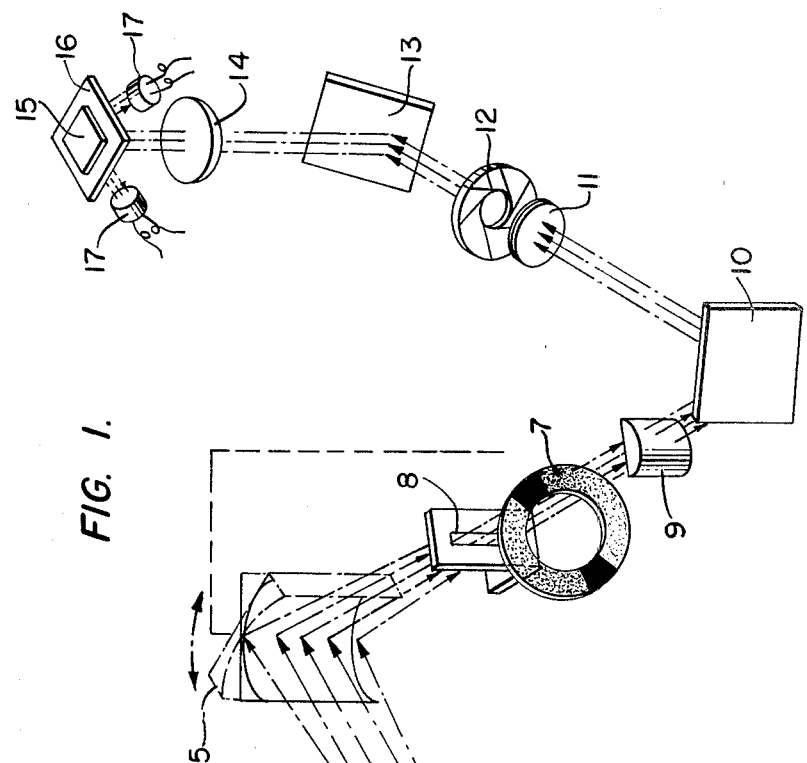
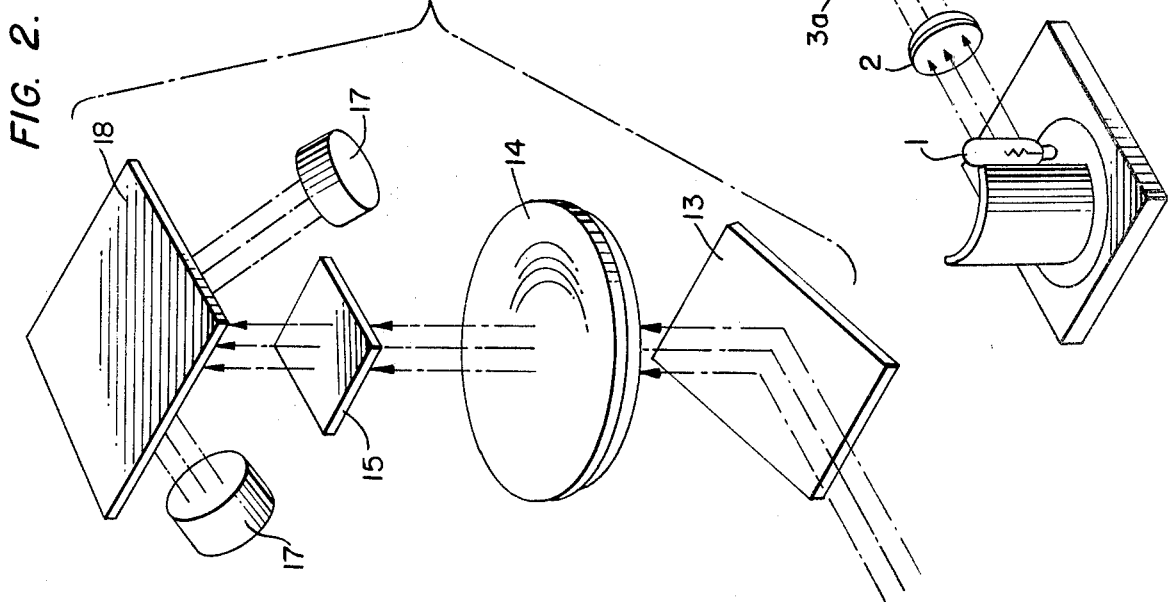
FIG. 1.
FIG. 2.

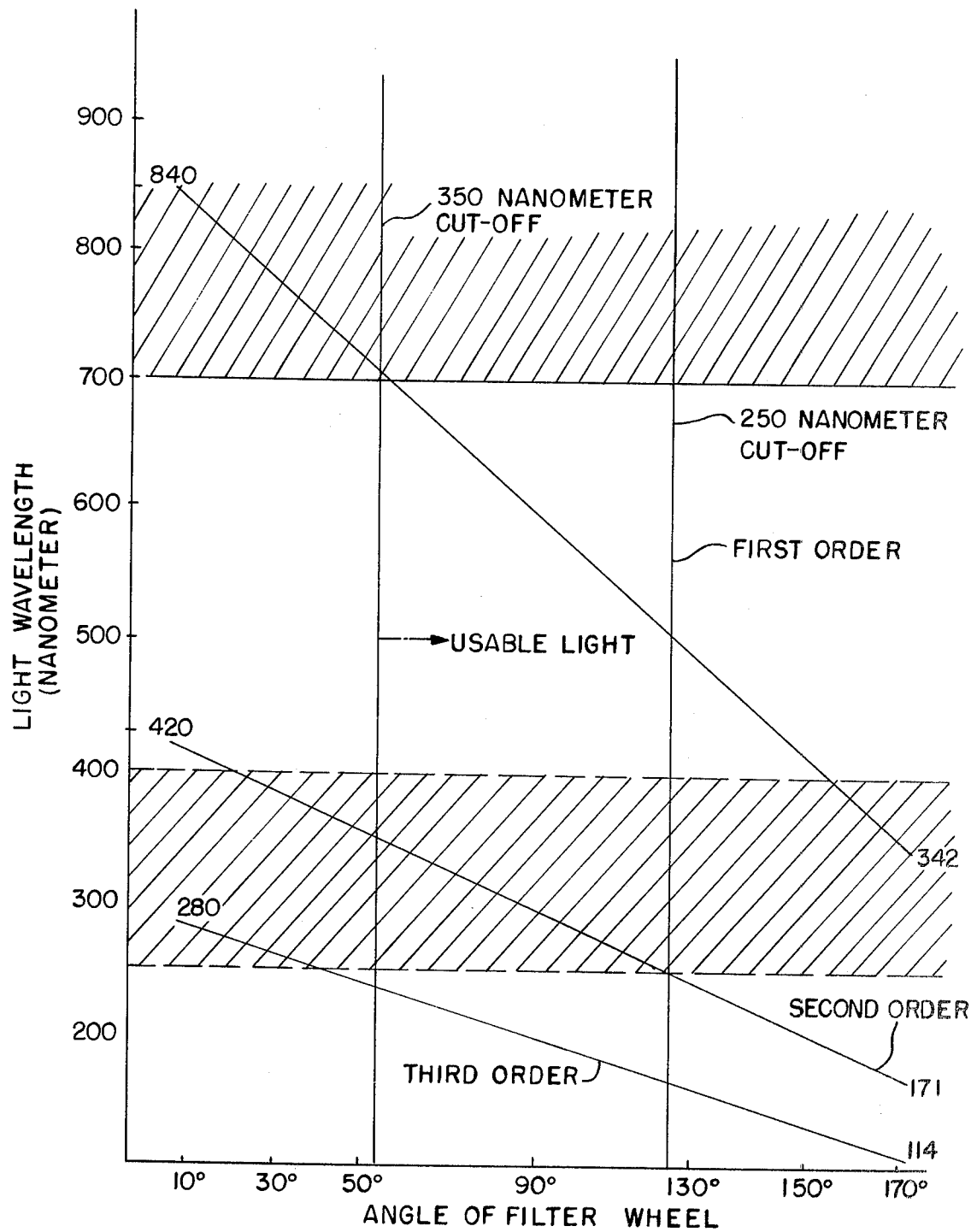

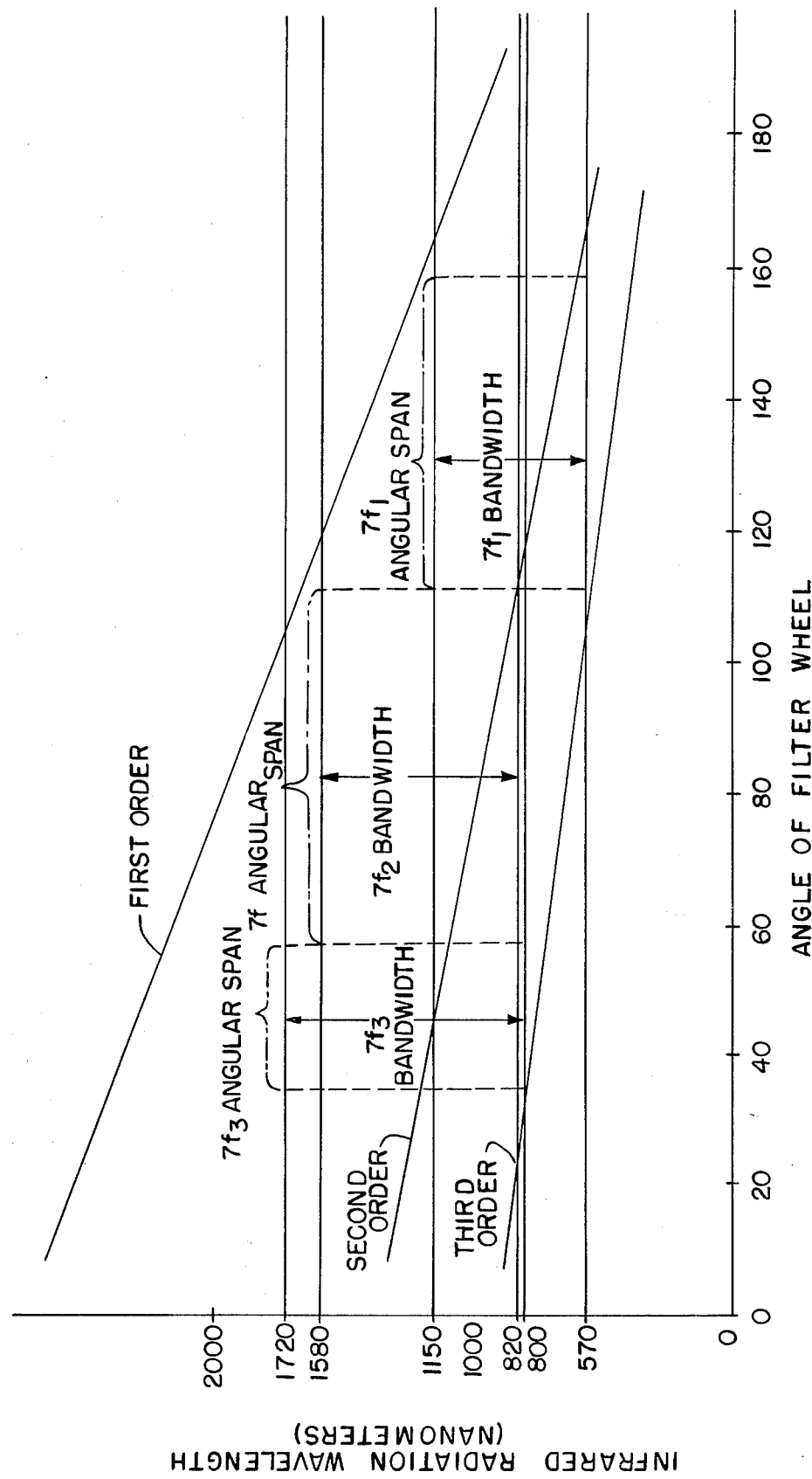

RAPID SCAN SPECTRAL ANALYSIS SYSTEM UTILIZING HIGHER ORDER SPECTRAL REFLECTIONS OF HOLOGRAPHIC DIFFRACTION GRATINGS

CROSS REFERENCE TO RELATED APPLICATION

The present application is a continuation-in-part of copending application Ser. No. 825,155, filed Aug. 15, 1977, by applicant entitled "*Holographic Diffraction Grating System for Rapid Scan Spectral Analysis*" and assigned to the assignee of the present application.

BACKGROUND OF THE INVENTION

The present invention relates generally to the field of instruments for spectrally measuring and analyzing optical properties of samples and, specifically, to improved instruments utilizing first and second order spectral reflections for more accurate spectral analysis. Such instruments are presently used in industrial and agricultural applications for colorimetry and for quantitatively analyzing the constitutents of samples. Additional applications for such instruments are being developed in the field of medicine in which samples are spectrally analyzed for diagnostic purposes.

Examples of agricultrual applications presently in use are instruments which accurately determine the oil, protein and water content in grain or soy beans. The traditional analytical laboratory techniques, such as the Kjeldahl technique for measuring protein, are extremely accurate but require the services of a skilled chemist. The results, furthermore, are not immediately or readily available. Buyers of agricultural products have demonstrated an increasing interest in accurate and rapid determinations of the moisture, protein and oil percentages of the various products purchased. The wheat export market, for example, has seen the widespread introduction of selling on the basis of guaranteed protein content. This competitive pressure has increased the requirement of the commodity handler, from the country elevator to the export terminal, to rapidly and accurately sort grains and other products by their protein percentage, as well as by oil and water content, where applicable. The need for versatile, yet low cost, advanced equipment, which combines and improves upon recent scientific findings in the field of nondestructive testing of agricultural products has greatly increased. For maximum usefulness of commodity handlers, such an instrument must not place high demands on the skillfulness of the operator or require a specialized knowledge of the scientific basis for the end result.

Recent developments have provided instruments which are able to satisfy the requirements of commodity handlers. The optical analyzer described by Donald R. Webster in U.S. Pat. No. 3,861,788, assigned to the assignee of the present application, provides an automatic test instrument for gauging the percentage of various constitutents in organic substances by comparing the reflective optical density of the sample at various wavelengths. This device contains narrow band optical filters connected together in the form of a rotatable paddlewheel positioned so that the filters can be individually swept through the incident light path between the specimen and a wideband light source. As the filter wheel turns, the band of light passed by each filter is progressively shifted with the changing angle of the filter relative to the light path. The filter wheel configuration includes opaque vanes extending from the ends of the filters to periodically interrupt the passage of light to the specimen. Photodetectors are positioned to sense the level of light reflected from the specimen. The output of these photodetectors is sampled at predetermined times relative to the rotation of the filter wheel to yield values indicative of reflected intensity at certain wavelengths. An electronic circuit utilizes this data to calculate three optical density difference values corresponding to moisture, protein and oil content of the specimen sample. The difference values are automatically inserted into three linear equations which are solved to obtain readings representing the three precentages of oil, water and protein content of the specimen.

A related, but earlier, instrument is described by Eugene R. Ganssle and Donald R. Webster in U.S. Pat. No. 3,765,775, entitled "*Optical Internal Quality Analyzer*", and also assigned to the assignee of the present application. The specimen sample therein is illuminated with light sequentially filtered by a continuously rotating disc carrying a plurality of narrow bandwidth optical interference filters. The combined output of several photodetectors positioned to receive light transmitted through or, alternatively, reflected by the specimen is selectively sampled after passing through a logarithmic amplifier to obtain readings at two discrete wavelengths which are then compared in a differential amplifier to provide the required measurements.

Yet another recent prior art photo-optical technique for determining, for example, the fat content of meat is described by George F. Button and Karl H. Norris in U.S. Pat. No. 3,877,818 owned by the United States of America. This technique, developed at the U.S.D.A. Agricultural Research Service in Greenbelt, Maryland, utilizes an instrument wherein a meat sample is exposed to infrared radiation from an incandescent light source. The radiation is transmitted through or reflected from the meat sample onto a tilting mirror which causes the respective transmitted or reflected light from the meat to pass through a planar interference filter at varying angles of incidence. Varying the angle of incidence of the filter by oscillating the tilting mirror produces a corresponding change in the wavelength of the radiation passing through the filter over a narrow bandwidth in the infrared spectrum. A photodetector receives the light transmitted through the filter and generates an electrical signal that is processed to read the fat content of the sample.

SUMMARY OF THE INVENTION

The instrument which is described in copending application Ser. No. 825,155 is designed for use both in colorimetry and in constituent analysis applications. This instrument improves upon the above prior art optical analyzers by providing a novel optical system which achieves greater accuracy at high speed and permits analysis of darker samples than was possible with the prior art high speed systems. In the instrument, a concave holographic diffraction grating oscillated at high speed is utilized to provide a rapid scanning of the monochromatic light produced at varying wavelengths by the grating. In a concave holographic grating, the lines of the grating are formed by a holographic technique. Concave holographic gratings are presently available on the market and are marketed by J-Y Diffraction Gratings, Inc. of Metuchen, New Jersey.

The holographic grating in the instrument of the copending application is made to oscillate at very high speed by means of a novel cam drive structure. The cam drive employs two identically shaped conjugate cams to provide positive drive of the grating in both directions. Each cam has a shape selected to make the grating wavelength output vary linearly with the angular position of the shaft driving the grating. The cam shape permits different gratings to be used with the same cam drive for different wavelength ranges.

The grating disperses light radiation directed at it through an entrance slit into spectral components which are focused along a circle drawn through the entrance slit and the grating. The circle along which these spectral components are in focus is known as a Rowland circle. The exit slit is positioned such that each respective spectral component dispersed by the grating is optimized for best focus and minimum aberrations at the exit slit as the grating is oscillated to scan the wavelength range.

Because the holographic grating is oscillated at very high speed, a rapid scan technique is possible enabling the instrument to eliminate noise by averaging over a large number of cycles. A filter wheel rotated synchronously with a cam drive is provided in the path of light passing through the exit slit. The filter wheel has two opaque segments arranged 180 degrees apart and which are rotated into the path of light passing through the exit slit when grating reaches its extreme positions in the oscillation cycle.

The filter wheel disclosed in the prior copending application Ser. No. 825,155, in addition to limiting stray light, also eliminates second order light and higher order light reflected by the grating, second order light being one-half the wavelength of the primary or first order light transmitted. For example, if light is being directed through the slit at 800 nanometers in wavelength by the grating, there will also be some light passing through the slit at 400 nanometers (second order) and some light at 267 nanometers (third order).

In accordance with the present invention, the spectral range of the instrument is broadened by utilizing both first order and second order light from the grating. This is accomplished by modifying the filter wheel disclosed in the aforementioned application Ser. No. 825,155. In the embodiments of the invention, operation in the visible-ultraviolet light range, half of the wheel will be the same as in the prior application and comprises an arcuate filter extending through a little less than 180 degrees with a continuously varying narrow bandwidth from one end to the other. The other arcuate half of the filter wheel, however, is modified to employ a special ultraviolet bandpass filter. The filter wheel is designed so that the bandpass filter transmits only second order light without transmitting any first order light or any third or higher order wavelength light.

The entire bandwidth of the second order light cannot be used because otherwise some first and third order light would also be transmitted by the bandpass filter. For example, as the range of first order light being directed through the exit slit by the grating varies between 342 and 840 nanometers in wavelength, the second order light directed throught the exit slit by the grating will vary between 171 and 420 nanometers in wavelength. Although the bandpass filter has a very sharp cutoff at the low and high ends spanning part of the second order range, it will also transmit light above 700 nanometers. Thus, when second order light to the exit slit above 350 nanometers is being transmitted by the grating, the exit slit will also receive first order light above 700 nanometers which would be transmitted by the bandpass filter. For this reason, no use is made of the second order light above 350 nanometers in wavelength. This does not affect the range of the system since first order light down to 342 nanometers in wavelength is used. The bandpass filter which transmits the second order light cuts off below 250 nanometers. Thus, light in the visible-ultraviolet spectrum range between 250 and 840 nanometers in wavelength may be transmitted by the filter arrangement of the present invention, thereby broadening spectral range of the instrument.

When a holographic diffraction grating which disperses infrared radiation is utilized for infrared analysis of a sample, an arcuate filter of continuously varying bandwidths is not utilized in the filter wheel. Instead, for first order light, a single, relatively wide, bandpass filter is employed on one-half of the wheel. The other half of the wheel is separated from the first by opaque segments as described above. The other arcuate half utilizes three separate bandpass filters, the cutoffs of which are selected and the filters are positioned so as to avoid transmitting first order light, third order light, and higher order light.

In addition, in the infrared spectral analysis system, different types of photodetectors are utilized for first and second order light because the detectors will respond to light in a limited range only. Silicon detectors are employed for detecting second order light and lead sulfide detectors for first order light. Switching between detectors is accomplished by means of a shaft encoder which responds to the shaft driving the oscillating grating as well as the rotating filter wheel and occurs when the opaque segments of the wheel pass the exit slit. The output from the silicon detector feeds directly into a logarithmic amplifier while the output of the lead sulfide detector goes first to a thermal drift correction amplifier circuit and then to a logarithmic amplifier. Switching between the outputs of the detectors is accomplished from the output of two logarithmic amplifiers.

Further objects and advantages of the present invention will become apparent by reference to the following detailed descriptions of the preferred embodiments considered in conjunction with the accompanying drawings.

BRIEF DESCRIPTION OF THE DRAWINGS

FIG. 1 is a schematic perspective view of one embodiment of the present invention utilizing an oscillating holographic grating and filter wheel wherein monochromatic radiation reflected by the sample is detected for spectral analysis;

FIG. 2 is a diagrammatic illustration of a modification of FIG. 1 wherein monochromatic radiation transmitted through the sample is detected for spectral analysis;

FIGS. 8 and 9 are graphic illustrations of wavelength transmissions of the filter wheel of FIGS. 5 and 6, respectively, for visible-ultraviolet light and infrared analysis.

DETAILED DESCRIPTION OF THE PREFERRED EMBODIMENT

Figure 3:
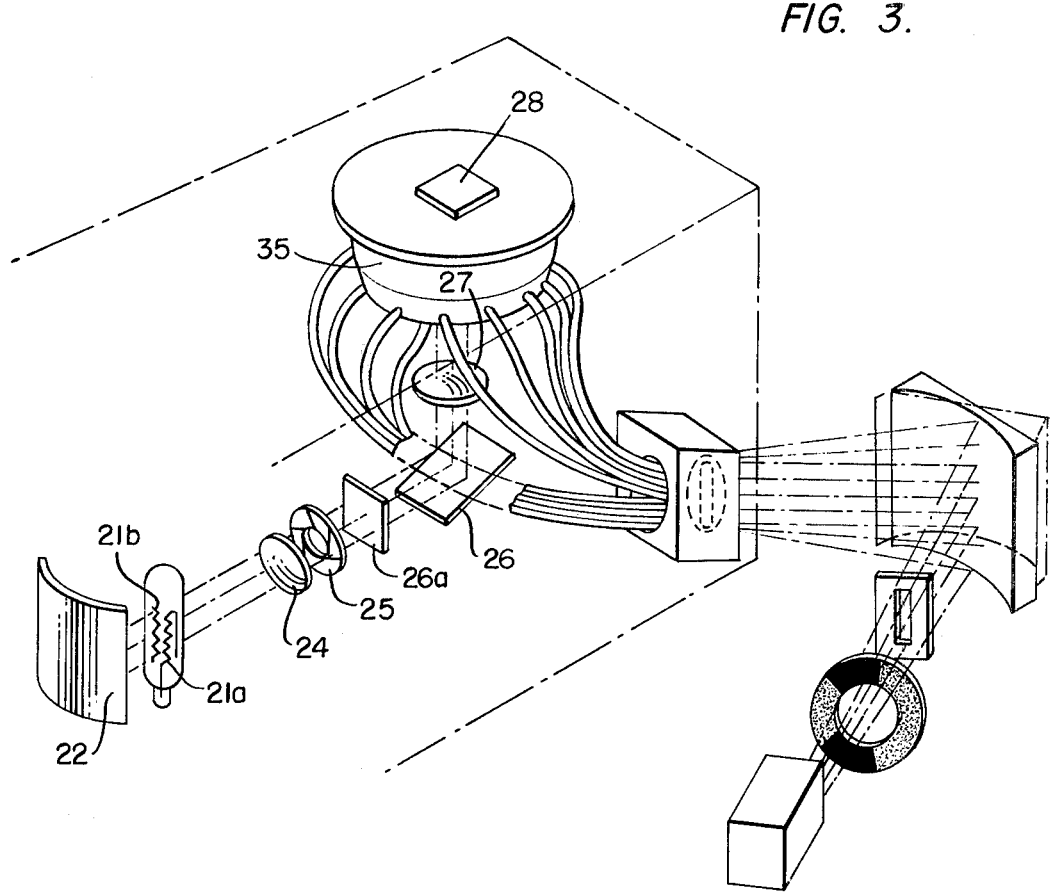
FIG. 3 is a perspective view of another embodiment of the present invention utilizing an oscillating holographic grating wherein white illumination reflected from a sample is collected by fiber optics and transmitted to the grating for dispersion and detection for spectral analysis.

In the schematic illustration of FIG. 1, the spacings of some of the components of the system has been exaggerated to facilitate illustration. As shown in FIG. 1, a tungsten filament light bulb source 1 emits wide band white light. The light from the tungsten filament is collected by a spherical lens 2 and is imaged on an entrance slit 4. A cylindrical lens 3 assures proper filling illumination of the concave holographic diffraction grating of the system designated by reference number 5. The lens 3, while shown spaced from the slit 4, will actually be positioned immediately adjacent to the slit 4.

A polarizer 3b for linearly polarizing the light may be provided in the light path between an infrared filter 3a and the cylindrical lens 3. The polarizer may be rotated about the optical axis through 90 degrees so that the axis of polarization can be varied. The polarizer, which serves to make possible irradiation of the sample with polarized light, is useful in constituent analysis applications in which the axis of polarization will be selected experimentally to give the most accurate determinations of the constituents of the sample.

Novel source optics, as described in greater detail in copending application Ser. No. 825,155, is employed to effectively double the length of the tungsten filament 1 so that a linear filament light source is provided which will approximately correspond to the aspect ratio of the entrance slit 4. The spherical lens 2 forms an image of the increased filament length on the entrance slit 4 to completely fill the entrance slit 4 with illumination. The axis of curvature of the cylindrical lens 3 is horizontal and this lens serves to focus the vertical dimension of the spherical lens 2 on the grating 5 so as to make the vertical dimension of the illumination on the grating correspond to the height of the grating. The infrared filter 3a is employed to filter out infrared light and reduces stray source light and unnecessary heat energy produced by the light source. Alternatively, a filter may be utilized in place of infrared filter 3a to pass infrared radiation when the grating and other components of the optical system are chosen for infrared analysis of the sample.

The grating 5 is a concave holographic grating of the type discussed above which is made to oscillate at very high speed in both directions, as generally indicated by the arrow in FIG. 1, by a cam drive structure which is described in greater detail in copending application Ser. No. 825,155. The oscillation of the grating 5 is synchronized with the rotation of a filter wheel 7 about its axis, the synchronization being schematically represented in FIG. 1 by the dashed line from the grating 5 to the filter wheel 7.

The holographic grating 5 disperses the white illumination imaged on it through the entrance slit 4 into spectral components which are focused at the exit slit 8. Alternatively, a holographic grating which disperses infrared radiation may be employed when infrared analysis of the sample is contemplated.

A cylindrical lens 9, the axis of curvature of which is vertical as distinguished from the cylindrical lens 3 wherein the curvature axis is horizontal, virtually images the width of the exit slit 8 back on the grating 5. Because the width of the exit slit 8 imaged on the grating 5 and the height of the grating are constant regardless of the oscillation of the grating, constant size illumination of a sample with the light dispersed by the grating can be efficiently achieved even though the grating is oscillating. The oscillation of the grating 5 will vary the wavelength but not the size or shape of the illumination on the sample.

The projection of the constant size monochromatic illumination is accomplished by means of the additional lenses and mirrors illustrated in FIG. 1 comprising the unique output optics of this preferred embodiment. Since the cylindrical lens 9 has provided an image of the width of the exit slit 8 on the grating 5, an image object is formed at the grating comprising a composit of the grating height and the virtual image of the exit slit width. After the beam of light passes through the filter wheel 7, it is reflected by mirror 10 to a spherical lens 11. The spherical lens 11 forms a real image of the composit of the slit width and grating height at a variable aperture iris 12. Because the width of the slit is constant and the height of the grating is constant, the real image formed at the iris aperture 12 will be of constant size. If the cylindrical lens 9 were not present, the image formed at the iris aperture 12 would vary in width as the grating changes its angular position. By changing the size of the opening (F-stop) of the iris aperture 12, the amount and size of illumination from the real image so produced at the iris 12 for illuminating the sample 15 can be controlled. The illumination from the image formed at the iris 12 is then reflected by a mirror 13 to a spherical lens 14, which takes the image that was formed at the iris 12 and focuses it on the sample 15 which has been positioned on a supporting plate 16. Because the image at the iris 12 is of constant size, the image on the sample will be of constant size. The light diffusively reflected from sample 15 is then sensed by photodetectors 17 for spectral analysis.

FIG. 2 illustrates a modification of the preferred embodiment in FIG. 1 wherein sample 15 is positioned to permit the monchromatic illumination to be transmitted through the sample. The illumination from the iris 12 is reflected by the mirror 13 and focused by the spherical lens 14 through the sample 15 on a diffusive white reflector 18. The radiation transmitted by the sample 15 is reflected by the white reflector 18 and sensed by the photodetectors 17 for subsequent spectral analysis of the sample. Alternatively, the sample 15 may be positioned adjacent to the variable aperture iris 12 so that illumination passing through iris aperture 12 and transmitted through the sample 15 will be subsequently sensed by the photodetectors 17.

Figure 5:
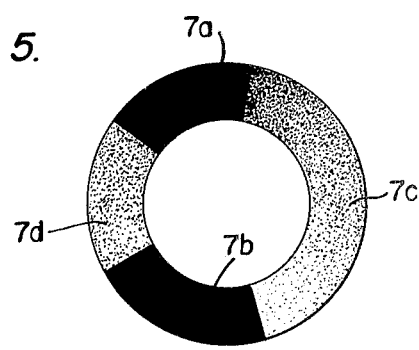
FIG. 5 is an illustration of the segmented filter wheel utilized in the present system for spectral analysis with visible and ultraviolet light.

The filter wheel 7 shown in FIG. 1 is driven by a motor so as to be synchronized with the oscillation of the grating 5. In FIG. 5, a plan view of the filter wheel 7 employed for visible-ultraviolet light transmission is illustrated. The filter wheel 7 has two dark or opaque segments 7a and 7b arranged 180 degrees apart and two circular or arcuate filter segments 7c and 7d running between the two opaque segments. The synchronization of the rotation of the filter wheel with the grating oscillation is such that the opaque segments 7a and 7b pass by the exit slit when the grating is in its extreme positions of oscillation so that one revolution of the filter wheel corresponds with one cycle of oscillation of the grating. The side of the filter wheel containing the filter segment 7c will pass by the exit slit while the grating moves from one extreme position to the other and the side containing the filter 7d will pass by the exit slit on the return half cycle of the grating oscillation when it moves from the other extreme position back to the one extreme position.

Filter segment 7c is a narrow bandwidth filter having linearly changing wavelength transmission bands such that the portion of this segment closer to the top of the filter wheel 7 will pass higher wavelengths than that position closer to the bottom of the filter wheel. The narrow bandwidth of segment 7c permits only first order light directed by grating 5 through the exit slit to be transmitted. For example, the present system contemplates transmission of first order light between 342 and 840 nanometers. At a given angle of the grating 5 in its oscillation cycle, the light reflected by the grating will be at a specific first order wavelength, plus some light at a second order wavelength which is one-half the first order wavelength, plus some light at a third order wavelength which is one-third the first order wavelength and so on for higher orders. Since filter segment 7c is a linearly changing narrow bandwidth filter, no second, third, or higher order wavelength light will be transmitted through this segment. Only first order light between 342 and 840 nanometers will be transmitted by this segment.

In the present system, it is desired to also utilize second order light below 350 nanometers to expand the spectral range for sample analysis. The arcuate filter segment 7d is therefore designed to have an operative position which transmits second order light without transmitting either first order light or any third or higher order light on the return half cycle of the grating oscillation.

The entire bandwidth of second order light cannot be used because otherwise some first order light, as well as some third or higher order light would also be transmitted. Since the first order light directed by the grating through the exit slit ranges from 342 to 840 nanometers, the second order light that is directed through the exit slit ranges from 171 to 420 nanometers. When the grating 5 is directing first order light of 700 nanometers through the exit slit, for example, it will also direct second order light of 350 nanometers through the exit slit. The filter segment 7d is made of Corning UV black glass, which is selected because it has a very sharp cut-off at the low and high ends spanning much of the second order range. The filter glass of filter 7b transmits in a bandwidth between wavelengths of 250 nanometers and 400 nanometers. The glass, however, also transmits light above 700 nanometers. For this reason, no use is made of the second order light directed through the exit slit by the grating longer than 350 nanometers in wavelength. However, there is no need to make use of second order light greater than 350 nanometers in wavelength since first order light is directed by the grating through the exit slit and is transmitted by the filter 7c down to 342 nanometers in wavelength. Accordingly, the filter 7d needs to span only that portion of the filter wheel which passes by the exit slit when second order light in the range of 250 to 350 nanometers in wavelength is being transmitted by the grating through the exit slit. In other words, the opaque segment 7a may extend far enough in the counterclockwise direction, as viewed in FIG. 5, to block second order light above 350 nanometers and the opaque segment 7b may extend far enough in the clockwise direction, as viewed in FIG. 5, to block second order light below 250 nanometers. The angular segment needed to be spanned by the segment 7d is about 70 degrees.

The fact that no use is made of second order light above 350 nanometers also avoids any problem with transmission of third order light, which would otherwise be transmitted by the filter glass of the second order filter 7d when the grating is transmitting second order light above 375 nanometers in wavelength through the exit slit.

FIG. 8 graphically illustrates the transmission of light by the grating through the exit slit as a function of the angular position of the filter wheel, which is synchronized with the grating oscillation. The line labelled "First Order" extending between 342 and 840 nanometers represents the wavelength of the first order light transmitted through the exit slit by the grating as the filter wheel rotates between 9 and 171 degrees carrying the second order filter 7d past the exit slit, zero and 180 degrees corresponding to the extreme positions of the grating. Similarly, the lines labelled "Second Order" and "Third Order" represent the transmission of second and third order light through the exit slit by the grating as the filter wheel rotates through this same angular range. Ths shaded area between 250 and 400 nanometers represents the transmission band of the second order filter 7d as does the shaded area above 700 nanometers. The vertical lines a and b represent the angular limits of the filter wheel between which the second order light is used and which must be spanned by the second order filter 7d. From the graph in FIG. 8, it will be seen that if it were attempted to use second order light greater than 350 nanometers, which is transmissible by the second order filter 7d, the filter 7d also at the same time would be transmitting first order light above 700 nanometers. Similarly, if it were attempted to use second order light above 375 nanometers, third order light above 250 nanometers would also be received through the exit slit and be transmitted by the filter 7d. For this reason, the upper limit of second order light used by the system is 350 nanometers. As a result, the visible ultraviolet spectrum of the system extends between 250 and 840 nanometers. This extended range is made possible by using the filter wheel of FIG. 5.

Figure 6:
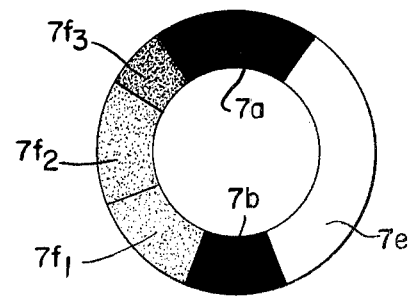
FIG. 6 is an illustration of the segmented filter wheel utilized in the present system for analysis with infrared radiation.

When infrared sample analysis is desired, the system of FIG. 1 is modified to employ an infrared diffraction grating and the filter wheel 7 illustrated in FIG. 6. As in the case of the filter wheel of FIG. 5, the infrared filter wheel has two opaque segments 7a and 7b arranged 180 degrees apart separating first order 7e and second order 7f arcuate filter segments. For first order infrared transmission, filter segment 7e is a simple bandpass filter rather than a filter of continuously varying bandwidth as in the case of segment 7c of FIG. 5. For second order infrared transmission, filter segment 7f is employed comprising three separate bandpass filters $7f_1$, $7f_2$, and $7f_3$.

As in the case of the visible-ultraviolet filter wheel, the filter wheel of FIG. 6 is rotated synchronously with the oscillation of the grating so that the opaque segments 7a and 7b of the filter wheel pass by the exit slit at the time the grating passes through the extreme positions in its oscillation cycle. The filter segment 7e thus passes by the exit slit during one-half cycle of the grating oscillation between its extreme positions and the filter segment 7f passes by the exit slit on the return half cycle of the grating.

With the infrared grating, the first order infrared radiation dispersed is in the range between 1080 and 2650 nanometers. At the same time, second order infrared radiation will be dispersed in the range between 540 nanometers and 1325 nanometers in wavelength. The system is designed to use only the first order light transmitted through the exit slit in the range of 1200 to 2400 nanometers in wavelength while the segment 7e is passing the exit slit and to use second order light in the range of 600 nanometers to 1200 nanometers while the filter segment 7f is passing the exit slit on the return half axle of the grating oscillation. The glass of filter segment 7e cuts off light below 1200 nanometers and transmits light above this range. The glass of filter segment $7f_1$ transmits infrared radiation in the bandwidth between 570 nanometers to 1150 nanometers in wavelength. It also transmits light above 1750 nanometers. The glass cuts off light below 570 nanometers and between 1150 and 1720 nanometers. This filter spans an annular segment on the filter wheel to receive second order light passing through the exit slit in the range between 600 nanometers and 830 nanometers. The glass of filter segment $7f_2$ will transmit light in the bandwidth between 820 nanometers and 1580 nanometers and above 2400 nanometers. It cuts off light below 820 nanometers and in the range between 1580 nanometers and 2400 nanometers. The filter segment $7f_2$ spans an angular segment on the filter wheel to receive second order light passing through the exit slit in the range of 830 nanometers to 1090 nanometers. The glass of the filter segment $7f_3$ will transmit light in the bandwidth of 800 nanometers to 1720 nanometers and will cut off light below 800 nanometers and above 1720 nanometers. The filter segment $7f_3$ spans an angular segment of the filter wheel to transmit second order light passing through the exit slit in the range of 1090 nanometers and 1200 nanometers.

The grating will vary the wavelength of the first order light directed through the exit slit between 1080 nanometers and 2650 nanometers as the filter wheel rotates through an angle of 162 degrees. The filter wheel will rotate through an angle of just 124 degrees as the wavelength of the first order light passing through the exit slit varies between 1200 and 2400 degrees, which is the portion of the first order light dispersed by the grating that is made use of by the instrument. Accordingly, the filter segment 7e needs to span an angle of only 124 degrees. The filter segment 7f needs to span the same angular range since it is designed to transmit second order light from 600 nanometers to 1200 nanometers, which is transmitted through the exit slit at the same time that first order light ranging from 1200 to 2400 nanometers is transmitted through the exit slit. The 124 degree segment spanned by the filter segment 7f will be symmetrical with respect to the segment spanned by the filter 7e about a line passing through the angular position of the filter wheel corresponding to the extreme positions of the grating.

The transmission characteristics and positioning of three filter segments 7f avoid transmitting first order or third and higher order infrared radiation. The first order filter segment 7e is selected to cut off all infrared radiation shorter than 1200 nanometers in wavelength to avoid any second order transmission while first order radiation is being utilized. If the filter segment 7e were extended to transmit first order light greater than 2400 nanometers in wavelength, the filter segment 7e would at the same time be receiving second order light greater than 1200 nanometers in wavelength which is above the lower cutoff on the filter 7e. For this reason, the usable range of the first order light is from 1200 nanometers to 2400 nanometers.

FIG. 9 is a graphic illustration of the wavelength transmissions of the infrared grating through the exit slit as a function of the angular position of the filter wheel. The line labelled "First Order" represents the transmission of the first order light through the exit slit by the infrared grating as the filter wheel rotates between 9 degrees and 162 degrees while the filter segment 7f is passing by the exit slit. The lines labelled "Second Order" and "Third Order" represent the wavelengths of the second order light and third order light directed by the infrared grating through the exit slit as the filter wheel rotates through this same angular range. The area between the horizontal lines at 570 nanometers and 1150 nanometers represents the transmission bandwidth of the filter $7f_1$; the area between the horizontal lines at 820 nanometers and 1580 nanometers represents the transmission bandwidth of the filter $7f_2$; and the area between the horizontal lines at 800 and 1720 nanometers represents the transmission bandwidth of the filter $7f_3$. The brackets labelled $7f_1$, $7f_2$, and $7f_3$ represent the angular segment spanned by each filter. As illustrated, the filter $7f_1$ spans an angular segment to receive second order light in the range of 600 nanometers to 830 nanometers, the segment $7f_2$ spans an angular segment to receive second order light from 830 nanometers to 1090 nanometers and the filter segment $7f_3$ spans an angular segment to receive second order light from 1090 nanometers to 1200 nanometers. From FIG. 10, it can be seen that if a broad band filter were used to transmit the entire range of second order light from 600 nanometers to 1200 nanometers, first order light would also be transmitted nearer the lower end of the range and third order light would be transmitted near the upper end of the range. By using three separate filter segments, as disclosed, the transmission is limited to second order light. It can also be noted in FIG. 10 that either the filter segment $7f_2$ or $7f_3$ could be used to transmit second order light in the entire range between 830 nanometers and 1200 nanometers. However, if the filter $7f_2$ were used for the entire range, it would transmit some first order light when it receives second order light near 1200 nanometers in wavelength because this filter glass begins to transmit light again at about 2400 nanometers and above. The filter $7f_3$ is not used to cover the entire range between 830 nanometers to 1200 nanometers because the glass of this filter is more expensive than the glass of the filter of $7f_2$. As a result of the arrangement of the filters on the filter wheel shown in FIG. 6 for use with the infrared grating, a range for the infrared system is provided between 600 nanometers and 2400 nanometers.

Figure 7:
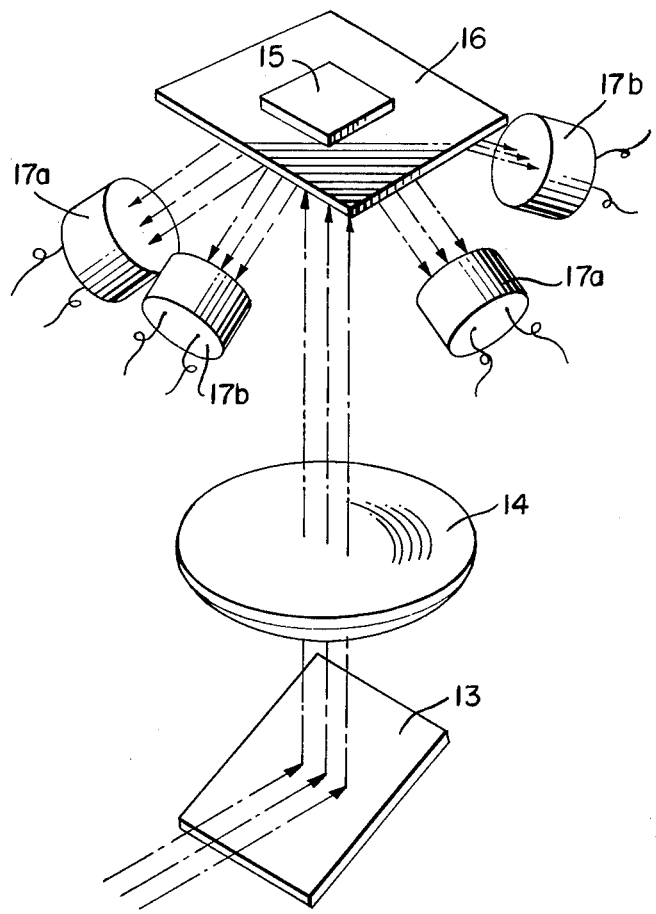
FIG. 7 is a diagrammatic illustration of the use of different photodetectors for detecting first and second order transmissions through the filter wheel for infrared analysis.

FIG. 7 illustrates the photodetector arrangement utilized in the infrared system. Two sets of detectors 17a and 17b are employed, silicon detectors 17a being used for detecting second order infrared radiation and lead sulfide detectors 17b being used for first order radiation. The different types of detectors are needed because each responds only to a limited wavelength range. Switching between detectors 17a and 17b occurs during the dark period when the opaque sections 7a and 7b of infrared filter wheel 7 of FIG. 6 are in position to block the radiation passing through the exit slit.

Figure 10:
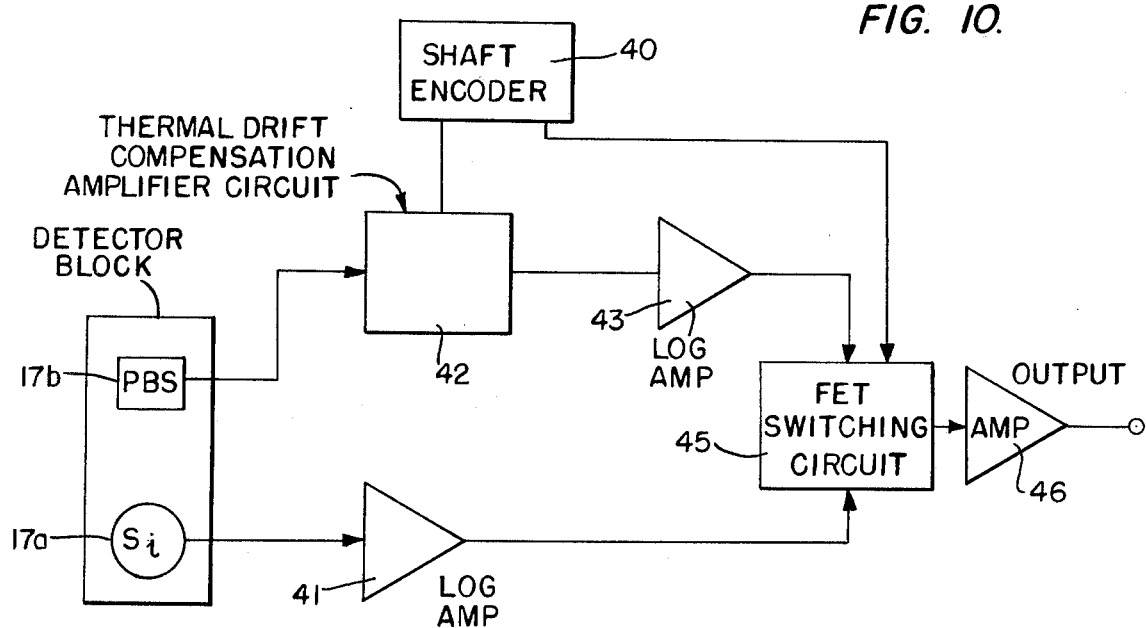
FIG. 10 is a block circuit diagram illustration of the infrared detection system for switching between the outputs of the photodetectors of FIG. 7.

Switching between the detectors is carried out in response to control signals from a shaft encoder 40, as shown in FIG. 10. Shaft encoder 40 is responsive to the angular position of the shaft (not shown), which drives the oscillating grating as well as the filter wheel, and produces control signals at selected angular positions of the shaft. The output of the silicon (second order) detectors 17a is fed directly into a logarithmic amplifier 41. The output of the lead sulfide (first order) detectors 17b is fed to a thermal drift compensation amplifier circuit 42 and then to a logarithmic amplifier 43. The circuit 42 automatically compensates for thermal drift of the lead sulfide detector 17b when the opaque segment 7b blocks the light passing through the exit slit just prior to when the filter segment 7e is moved into the path of the light passing through the exit slit as the filter wheel rotates in the clockwise direction as viewed in FIG. 6. This compensation is carried out in the same manner as described in the Webster U.S. Pat. No. 3,861,788 and specifically as carried out by the circuit disclosed in FIG. 5 of the patent. This compensation is initiated when the opaque segment 7b is in position in response to a control signal from the shaft encoder 40. Switching between the outputs of the first order detectors 17b and second order detectors 17a is effected by means of the FET electronic switch 45 which is controlled by the shaft encoder 40. When the filter wheel rotates clockwise so that the opaque segment 7a is in position to block the radiation passing through the exit slit, a control signal from the shaft encoder will cause the FET circuit 45 to switch from the output of the logarithmic amplifier 43 to the output of the logarithmic amplifier 41. Similarly, when the opaque segment 7a rotates into position to block the exit slit, as the filter wheel rotates in the clockwise direction, the control signal from the shaft encoder will cause the FET circuit 45 to switch from the output of the logarithmic amplifier 41 to the output of the logarithmic amplifier 43. The selected output is then fed to an output amplifier 46 where the signals are amplified and transmitted to an electronic analysis system.

A perspective view of another embodiment of the present invention is shown in FIG. 3. Wide band white light is projected by the optics shown to form a spot of illumination on sample 28. Since in this embodiment, the sample is to be illuminated by white light rather than the monochromatic illumination utilized in FIG. 1, the ideal shape of the illumination to be projected on the sample should be a spot or circle of light. Since tungsten filaments are not commonly formed in circular shapes, the present embodiment contemplates optically modifying the tungsten filament light source in order to achieve this goal. To this end, a reflector 22 is positioned as shown in FIG. 3 to form an image 21b of filament 21a along side of itself. The light source so formed is shaped as a square, which more nearly approximates the ideal shape of a circle than the linear filament. The square filament source is imaged by lens 24 on lens 27. The latter lens 27 in turn will project an image of the illumination at iris 25 on the sample. The variable aperture iris 25 is positioned adjacent to lens 24 to control the size of, and, therefore, the amount of illumination being projected on the sample. Mirror 26 is neccessary to "fold" the light illumination from the source upwards toward the sample. An infrared filter 26a is provided to reduce stray source light and unnecessary heat energy produced by the source. Alternatively, a filter may be utilized in place of infrared filter 26a to pass infrared radiation when the grating and other components of the optical system are chosen for infrared analysis of the sample as discussed above.

An advantage of using the two lenses 24 and 27, as described above, is that this arrangement produces a nearly round spot of light on the sample, which is variable in size. Because the shape of the light source by the operation of the reflector 22 producing an image of the filament next to itself has made it approximately square in shape, the illumination passing through the lens 24 will substantially fill the lens 24. As a result, when the lens 27 focuses an image of the iris which is adjacent to lens 24 on the sample 28, it produces an almost uniform round circle of light on the sample.

The novel source optics for approximating a circular light source is described in greater detail in copending application Ser. No. 825,155. The circle or spot of light projected on sample 28, which has been positioned on a supporting plate 34 by means of the optics described above, is diffusively reflected by sample 28. The reflected illumination is collected by the endfaces of a fiber optics array 29 which is comprised of a plurality of individual fiber bundles arranged at one end on a conical locus to receive reflected illumination from the sample. The ends of the fiber bundles are mounted in a conical support member 35 which may be made transparent to reduce the amount of stray light reflected by the support member. At the other end, the ends of the fiber bundles of the fiber optics array are arranged linearly to form an entrance slit 30. Light reflected by sample 28 is, therefore, effectively transmitted through the fibers by internal reflection to completely fill the entrance slit 30. The optical parameters of the fiber optic array 29 are chosen such that each fiber accepts a cone of light reflected by the sample 28 which is equal in angle to the acceptance cone of the grating 31.

The light exiting from the linear endface 30 formed by the fiber optics array 29 will, therefore, project the light transmitted by the array 29 on the grating 31 at an angle which will permit the light to completely fill the grating 31 with all the light illumination accepted and transmitted by the fiber optic array 29. This improved design utilizing the fiber optics array 29 permits optimum utilization by the grating 31 of the light intensity reflected by the sample 28 and transmitted through the fiber optics 29.

The grating 31 in this embodiment is also oscillated at very high speed as described earlier in connection with the embodiment of FIG. 1 and provides rapid scanning of the spectral light dispersed at an exit slit 32. The monochromatic light passing through exit slit 32 is sensed by photodetector 33 for spectral analysis of the sample.

When visible light spetral analysis is employed, a filter wheel 7 of the identical structure as the filter wheel 7 of FIG. 5 is positioned immediately after the exit slit 32 in FIG. 3. Filter wheel 7 is synchronized with the oscillation of grating 31 for the identical purpose as was filter wheel 7 in FIG. 1 discussed earlier.

When infrared radiation analysis is employed, the filter wheel 7 of FIG. 6 is positioned immediately after the exit slit 32 in FIG. 7. The infrared filter wheel 7 is likewise synchronized with the oscillation of the infrared grating 31 for the same purpose as was the filter wheel 7 in FIG. 1 for infrared analysis.

Likewise, two sets of detectors (silicon and lead sulfide) are utilized instead of a single detector 33 in FIG. 3 when infrared analysis is employed for sensing alternatively first and second order infrared radiation as explained earlier. Switching between detectors is accomplished in a manner similar to that described above in connection with the block diagram circuit of FIG. 10.

Figure 4:
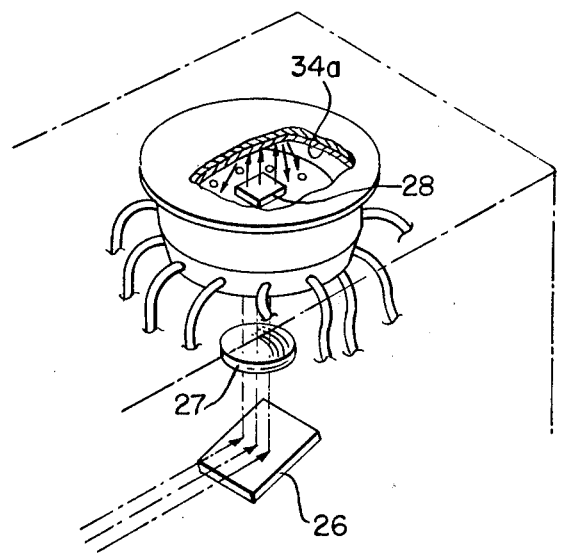
FIG. 4 is a diagrammatic illustration of a modification of FIG. 3 wherein the fiber optics collects the illumination which is transmitted through the sample.

The embodiment of FIG. 3 can be further modified to detect radiation transmitted by the sample as shown in FIG. 4. The sample 28 is so arranged that the spot of source light transmitted through sample 28 is reflected by a diffusive white reflector 34a. The reflected light is then collected by the endface of the fiber optic array 29, as described in connection with FIG. 3, and is transmitted through individual fibers of array 29 by internal reflection to their opposite ends forming entrance slit 30. The operation is then exactly the same as described in connection with FIG. 3 above The output from the system is in the form of an analog signal derived from the photodetectors. In the infrared system, this analog signal is the output from the amplifier 46. In the visible-ultraviolet system, the output signal is from a logarithmic amplifier connected to amplify the output of the photodetector. This output signal will correspond to the optical density, reflective or transmissive, of the sample at the specific wavelength irradiating the sample. An analysis of the sample may be carried out from the output signal in the manner disclosed in the U.S. Pat. No. 3,861,788. The output signal may be converted to digital representations and the digital representation produced at selected angular positions of the filter wheel may be stored in a computer, which would also receive signals from the shaft encoder indicating the angular position of the filter wheel and, accordingly, indicating the wavelength of irradiation for each stored digital representation. Analysis of the sample can then be carried out by mathematical operations performed by the computer on the stored digital representations.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. Optical apparatus for analysis of a sample, comprising a diffraction grating operable to disperse impinging infrared radiation into narrow bandwidth components, means to oscillate said diffraction grating, optical means for projecting radiation on the oscillating grating, an exit slit positioned to receive radiation dispersed by said grating, a filter wheel located in the path of said dispersed radiation having a first radiation transmitting section and a second radiation transmitting section, means to rotate said filter wheel in synchronism with the oscillation of said grating whereby said first transmitting section moves through the path of radiation passing through the exit slit during the oscillatory movement of said grating from one extreme position to the other and rotates said second transmitting section into the path of the radiation passing through said exit slit during the oscillatory movement of said grating from said other extreme position to said one extreme position, said first transmitting section being adapted to transmit only first order light dispersed by said grating during at least a portion of the oscillatory movement of said grating from said one extreme position to said other extreme position, said second transmitting section being adapted to transmit only second order light dispersed by said grating during at least a portion of the oscillatory movement of said grating from said other extreme position to said one extreme position, and photosensing means for detecting radiation that has passed through said exit slit and the transmitting sections of said filter wheel.

2. An optical apparatus as recited in claim 1, wherein said first light transmitting section comprises a bandpass filter selected to cut off light transmission below a predetermined wavelength selected to prevent transmission of second order light through said bandpass filter.

3. An optical apparatus as recited in claim 1, wherein said second radiation transmitting section comprises a plurality of bandpass filters with different transmission bandwidths spanning different angular segments of said filter wheel.

4. An optical apparatus as recited in claim 3, wherein the cutoff limits of said bandpass filters and the angular segments spanned by said filters are selected so that each of said segments passes only second order light passing through said exit slit.

5. An optical apparatus as recited in claim 3, wherein said first light transmitting section comprises a single bandpass filter.

6. Optical apparatus as recited in claim 1, wherein said first light transmitting section has a varying optical effect on light radiation with different angular positions and wherein said second light transmitting section is a bandpass filter having a constant optical effect on light radiation at different angular positions.

7. Optical apparatus for analyzing a sample comprising a diffraction grating operable to disperse impinging infrared radiation into narrow bandwidth components, means to oscillate said diffraction grating, optical means for projecting the infrared radiation on the oscillating grating, an exit slit positioned to receive radiation dispersed by said grating, photosensing means for detecting radiation that is passed to said exit slit, a filter wheel located in the path of said dispersed radiation, drive means to rotate said filter wheel in synchronism with the oscillation of said grating, said filter wheel including a first radiation transmitting section adapted to transmit a first infrared wavelength range and a second infrared radiation transmitting section adapted to transmit a second infrared wavelength range, said filter wheel including nontransmitting segments positioned about 180 degrees apart which separate said first and second transmitting sections, said drive means positioning said nontransmitting segments to interrupt the radiation when said grating is at one of its extreme positions, said photosensing means comprising first detector means responsive to the radiation transmitting through said first radiation transmitting section and second detector means responsive to the radiation transmitting through the second radiation transmitting section, and electronic means to switch between said first and second detector means when each of said nontransmitting segments interrupts the radiation passing through the exit slit.

8. The optical apparatus of claim 7, wherein said first detector means comprises at least one lead sulfide photodetector and said second detector means comprises at least one silicon photodetector.

9. An optical apparatus comprising a diffraction grating operable to disperse impinging infrared radiation of a narrow bandwidth component, means to oscillate said diffraction grating, optical means for projecting radiation on said oscillating grating, an exit slit positioned to receive radiation dispersed by said grating, a filter wheel located in the path of said dispersed radiation having a first radiation transmitting section and a second radiation transmitting section, means for rotating said filter wheel in synchronism with the oscillation of said grating whereby said first transmitting section moves through the path of radiation passing through the exit slit during the oscillatory movement of said grating from one extreme position to the other and rotates said second transmitting section into the path of the radiation passing through said exit slit during the oscillatory movement of said grating from said other extreme position to said one extreme position, said first transmitting section being adapted to transmit only light of a predetermined order dispersed by said grating during at least a portion of the oscillatory movement of said grating from said one extreme position to said other extreme position, said second transmitting section being adapted to transmit only light of another order during at least a portion of the oscillatory movement of said grating from other extreme position to said one extreme position.

10. An optical apparatus comprising a diffraction grating operable to disperse impinging radiation to narrow bandwidth components, means to oscillate said diffraction grating, optical means for projecting radiation on the oscillating grating, an exit slit positioned to receive radiation dispersed by said grating, a filter wheel located in the path of dispersed radiation passing through said exit slit, said filter wheel having a radiation transmissive section comprising a plurality of adjacent bandpass filter segments, drive means to rotate said filter wheel in synchronism with the oscillation of said grating whereby said transmitting section moves through the path of radiation passing through said exit slit during the oscillatory movement of said grating from one extreme position to the other, each of said filter segments having a bandwidth broad enough to transmit more than one order of the radiation dispersed by said grating toward said exit slit as said grating oscillates from one extreme position to the other and broad enough to transmit a substantial portion of the wavelength range of a predetermined order dispersed by said grating as said grating oscillates from one extreme position to the other, said filter segments being angularly positioned on said filter wheel so that only said predetermined order of the light radiation dispersed by said grating passes through said light transmitting section and said exit slit during the oscillatory movement of said grating from one extreme position to the other.

11. An optical apparatus as recited in claim 10, wherein said light transmitting section comprises three adjacent bandpass filters, each transmitting radiation of a different wavelength range.

12. The optical apparatus of claim 10, wherein said filter wheel includes a second light transmitting section, said second light transmitting section being adapted to transmit only first order light and said first mentioned light transmitting segment being adapted to transmit only second order light.

* * * * *